United States Patent

Greenstein

[11] 4,060,897
[45] Dec. 6, 1977

[54] DEVICE FOR FORMING DENTAL RESTORATIONS

[76] Inventor: Jean Greenstein, 16844 Mooncrest Drive, Encino, Calif. 91436

[21] Appl. No.: 679,553

[22] Filed: Apr. 23, 1976

[51] Int. Cl.² .............................................. A61L 3/00
[52] U.S. Cl. ...................................... 32/40 R; 32/46
[58] Field of Search ....................... 32/40 R, 46, 51, 50

[56] References Cited

U.S. PATENT DOCUMENTS 550,508  11/1895  Howe ........................................ 32/50

OTHER PUBLICATIONS

Silvorman's Dental Catalogue, 1976 Edition, Plymouth Meeting, Pa. 19462, p. 23.

Primary Examiner—Robert Peshock
Attorney, Agent, or Firm—Robert J. Schaap

[57] ABSTRACT

A tool for forming dental restorations used in the oral cavity of a human being and which restorations are at least partially made of a synthetic restoration material, such as porcelain. The dental tool comprises an elongate handle section capable of being grasped by the fingers or a hand of the user thereof. A first tool section located on one end of the handle section is capable of performing a first operation in the formation of a dental restoration. A second tool section is located on the opposite end of the handle section and is cooperatable with the first tool section and used in the formation of the dental restorations from the synthetic material. These first and second tool sections are used in combination in very closely timed relationship in order to properly form the dental restorations. A serrated surface section, which functions as a vibrating member, is also located on the handle section intermediate the first and second tool sections. This serrated surface section is designed to create a vibratory action on the dental restorations during formation thereof through reciprocative movement of the tool in order to create fluid movement in the synthetic restoration material. The present invention also provides a method of using the tool for forming the dental restorations as well as a method of making the tool for forming these dental restorations.

28 Claims, 17 Drawing Figures

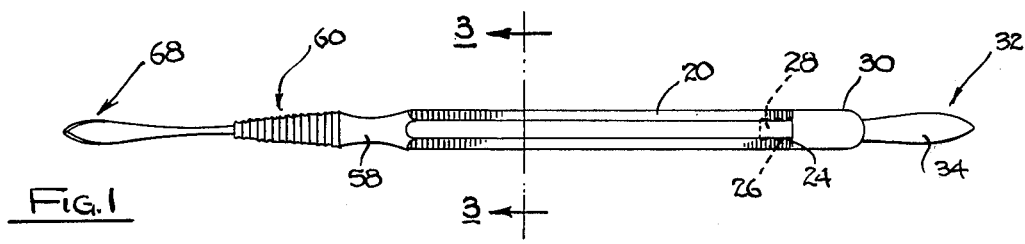
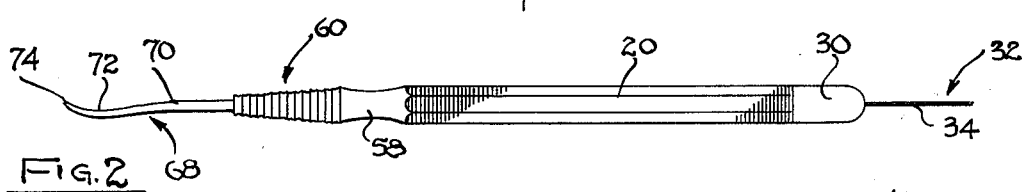
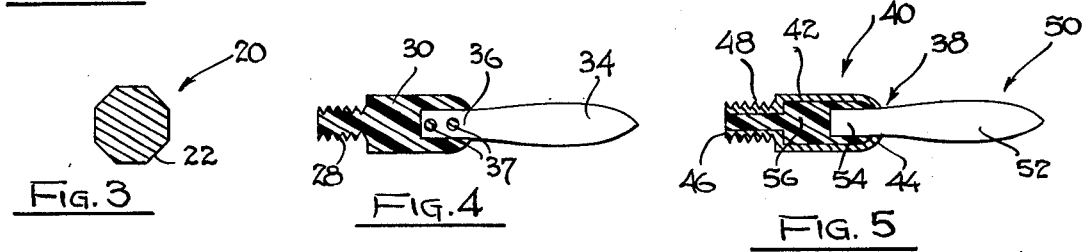
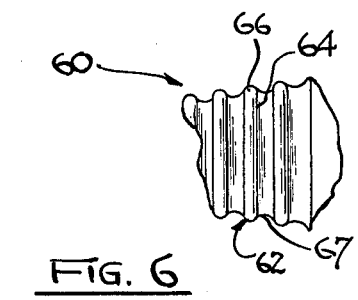
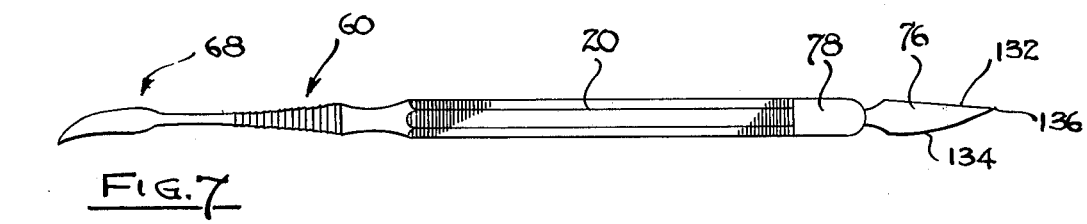
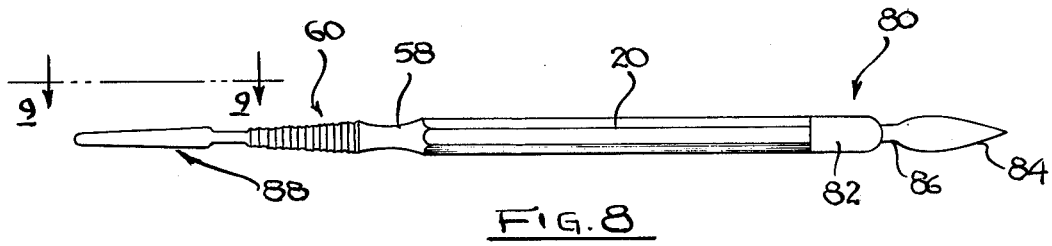

DEVICE FOR FORMING DENTAL RESTORATIONS

BACKGROUND OF THE INVENTION manipulatable

This invention relates in general to certain new and useful improvements in devices and methods used in the formation of dental restorations of the type used in the oral cavity of a human being, and, more particularly, to devices of this type which are easily manipulatable to perform a plurality of functions, as well as methods of using and making the same.

Dental restorations which are used in the oral cavity of a human being are usually constructed on a mold which becomes part of the dental restoration. These molds are typically formed of gypsum, a rather porous material which tends to absorb water. A metal frame is constructed around the gypsum mold and this metal frame is typically formed of a precious metal such as gold. Moreover, in the formation of the dental restoration, a restoration material is used to form the outer surface, and this restoration material is generally porcelain. The porcelain is applied to the metal framework around the gypsum mold and is thereafter baked on the framework.

It is fairly important that the porcelain restoration material be properly applied with the desired size and shape so as to resemble the appearance of a tooth normally appearing in the oral cavity. In addition, the dental restoration should be free from any small holes and like imperfections which would not only mar its appearance, but affect the quality and the life of the dental restoration. Other metals which may be used in addition to gold in the metal framework are platinum and palladium. It has been recognized that the metal oxides, particularly in the platinum and palladium, bond with the porcelain in order to form the dental restorations.

The porcelain restoration material, comprised mainly of feldspar, is a mineral substance containing aluminum oxide and silicon oxide, and may also contain potassium oxide, sodium oxide or calcium oxide. Feldspar is an effective restoration material since it is non-plastic and functions as an easily fusible binder. However, water is not missible with feldspar so that in any mixture of the feldspar and water, the water quickly settles out of or to the bottom of the feldspar-water composition. Nevertheless, in order to mold the feldspar, which is essentially the major component in the porcelain composition, it is necessary to have the water in the feldspar in order to render the same somewhat viscous to permit molding and shaping, as well as sizing of any composition produced therefrom. This is particularly true in the formation of dental restorations.

In the formation of the dental restorations in the past, the feldspar material has been mixed with the water and the producers of the dental restorations have attempted to work fairly quickly with a feldspar-water composition in order to permit the molding of the final dental restoration. If the water is allowed to settle from the feldspar-water composition, the porcelain can dry or "cure" fairly rapidly thereby preventing further working with the porcelain. This condition materially contributes to the difficulty in molding the porcelain into the desired shape and size. Moreover, this problem often results in a high loss rate of the work in progress. There have been several attempts to vibrate the dental restoration, or at least a portion thereof, during the formation of the restoration, in order to cause the feldspar to absorb the water and thereby permit easier molding thereof.

In the past, it was necessary for the technician to utilize several tools in order to form the dental restoration. One of these tools had a working end which was designed to pick up the porcelain from a source thereof and apply the same to a mold. Thereafter, another tool was utilized in order to pack the porcelain in a desired fashion. A third tool was necessary in order to shape the porcelain into the desired shape representative of a tooth in the oral cavity. Another tool was required in order to cut the porcelain and lift the same as may be desired. Several other tools were required in order to further shape the porcelain, compact, cut and perform other operations, in order to achieve the desired appearance. During the entire process, it was necessary to constantly create a vibratory action on the porcelain material, such that the porcelain material would hold the water, thereby enabling formation of the porcelain into the desired size and shape. In each case, the technician or other operator would use a tool or similar device to create the proper amount of vibratory action so that the water would temporarily be held by the porcelain during the vibratory action.

From the foregoing, it can be observed that one of the primary problems in forming the dental restorations encountered is the substantial time delays resulting from finding and selecting the proper tool for using the same in constructing the dental restoration. For example, if one of the tools which might be necessary at any step in the formation of the dental restoration is not immediately available, water would quick precipitate from the porcelain composition, thereby permitting the porcelain to set-up in a condition where it is not capable of being further molded. This resulted in a complete loss of the partially completed restoration. This condition is fairly prominent inasmuch as the technician often encounters substantial delay in selecting the proper tool and, in addition, creating the vibratory action which is necessary to cause the feldspar to hold the proper amount of water.

OBJECTS OF THE INVENTION

It is, therefore, the primary object of the present invention to provide a tool for forming dental restorations used in the oral cavity of a human being and having a handle section with a pair of tool sections mounted thereon and with a serrated surface section located intermediate the pair of tool sections.

It is another object of the present invention to provide a tool of the type stated which is highly efficient in its operation and which can be constructed at a relatively low unit cost.

It is a further object of the present invention to provide a tool of the type stated in which one of the tool sections may be removably connected to the handle section of the tool.

It is an additional object of the present invention to provide a tool assembly of the type stated which includes a pair of cooperating tool sections for forming dental restorations used in the oral cavity, and in addition a serrated surface which is located for vibratory movement with respect to the restorations during formation thereof in order to create fluid movement in a restoration material used in the formation of dental restorations.

It is also an object of the present invention to provide a method of utilizing a tool in order to form dental restorations used in the oral cavity of a human being on a highly efficient basis, thereby reducing the reject rate and reducing the amount of scrap material.

It is still another object of the present invention to provide a method of the type stated where a pair of tool sections are located on opposite ends of a handle section and which are manipulatable to perform the required work function, as well as a serrated surface section which is located in desired relationship to each of the tool sections in order to create a vibratory movement on the restoration in order to create fluid movement in the restoration material.

It is another salient object of the present invention to provide a method of making tools used in the formation of dental restorations for use in the oral cavity and which method permits the making of such tools at a relatively low unit cost in a mass production operation.

With the above and other objects in view, my invention resides in the novel features of form, construction, arrangement and combination of parts presently described and pointed out in the claims.

SUMMARY OF THE DISCLOSURE

The present invention relates to a tool which is capable of forming dental restorations for use in the oral cavity of a human being. The tool generally comprises an elongate handle section which is capable of being grasped by the fingers of the user. A first tool section is located on a portion of this handle section, and, in preferred embodiments thereof, is located on one end of the handle section. This first tool section is used in the formation of dental restorations from a synthetic restoration material, such as porcelain. A second tool section is located on another portion of the handle section, and, in a preferred embodiment, is located on an opposite end of the handle section. This second tool section is cooperatable with the first tool section and is also used in combination therewith in the formation of the dental restorations from the synthetic restoration material. A serrated surface section is associated with the elongate handle section and is also located intermediate the first and second tool sections. This serrated surface section is used to create a vibratory action on the dental restoration through reciprocative movement to further aid in the formation of the dental restorations.

In a more preferred embodiment of the present invention, the first tool section is designed with a size and shape to pick up a synthetic restoration material and place the same in proper position on a mold in order to form a dental restoration. In addition, the second tool section is designed with a size and shape to carve and shape the restoration. Either one of these tool sections may be designed with a size and shape to lift the restoration material or to condense the restoration material.

The serrated surface section mentioned above is generally comprised of a plurality of upstanding axially spaced apart ridges which are separated by reduced groove portions. These ridges are formed by radially outwardly extending rings terminating in outer annular curved edge portions. The ridges are sequentially formed with constantly reducing radius from one end of the serrated surface section to the other end thereof.

The handle section in the tool of the present invention may preferably include a first threaded attachment means and the tool section includes a head portion with the head portion having a second threaded attachment means. The second threaded attachment means is cooperatable with the first attachment means to fixedly, but nevertheless removably, secure the head portion to the handle portion. The first tool section in this case is fixedly, and generally non-removably, attached to the head portion.

In one embodiment of the present invention, the first attachment means may comprise a threaded shank on the handle section and the second attachment means may comprise an internally threaded recess in the head portion. In another embodiment of the present invention, the first threaded attachment means may comprise an internally threaded recess in the handle section with the second threaded attachment means comprising a threaded shank on the head portion. In addition, and in similar embodiments of the present invention, the second tool section may also be threadedly attached to the handle section.

In some respects, it is desirable to form the handle section in a non-circular cross-sectional shape in order to facilitate handling thereof. In addition, the handle section may also be provided with a plurality of slightly reduced serrations in order to further facilitate the handling. The serrated surface which is used to cause the vibratory action in the most preferred embodiment of the present invention is located in closer proximity to one of the tool sections than to the other of the tool sections on the tool of the present invention.

The two tool sections are located at opposite ends of the handle section which is properly sized so that the tool may be easily and quickly rotated through approximately a 180° arc in order to utilize both the first and second tool sections. Moreover, the serrated surface section is located relative to the tool sections so that it may be quickly and easily located in proximity to the dental restorations to cause the aforementioned vibratory action thereon, without any substantial delay in moving from the tool section to the serrated section.

The present invention further provides a method of using the tool for forming the dental restorations used in the oral cavity of a human being. In this case, the method comprises the engaging of the handle section of the tool and locating at least the first tool section on one end thereof relative to a mold means to perform an operation in the formation of a dental restoration. Thereafter, the method includes the shifting of the position of the tool to be located in a position where the serrated surface section is in proximity to the dental restoration being formed. The serrated surface section is then moved on the restoration, preferably in a reciprocative manner, to cause movement of the fluid therein. Thereafter, the dental tool is rotated through an approximately 180° arc to locate the second tool section in proximity to the dental restoration in order to permit the second tool section to operate on the dental restoration.

The present invention further provides a method of making the tools for use in the formation of dental restorations used in the oral cavity of a human being. In this case, the method comprises the locating of a plurality of metal blank sections in a position to be formed with a handle section. The blanks, along with the handle sections thereon, are located in a position to form the serrated surface sections on each of the tools thereafter. The serrated sections are located in close proximity to one of the tool sections. In addition, the tools are provided with a first tool section on one end of the handle section and which first tool section is used in the formation of the dental restoration to be used in the oral cavity. A second tool section is then located on the other end of the handle section to be used in the formation of a dental restoration formed from a synthetic restoration material.

In a preferred aspect of the present invention, one of the tool sections is removably attached to the handle section. Also, the other of the tool sections may be integrally formed with the handle section. In another embodiment, both of the tool sections may be removably attached, preferably through threaded attachment to the handle section.

BRIEF DESCRIPTION OF THE DRAWINGS

Figure 10:
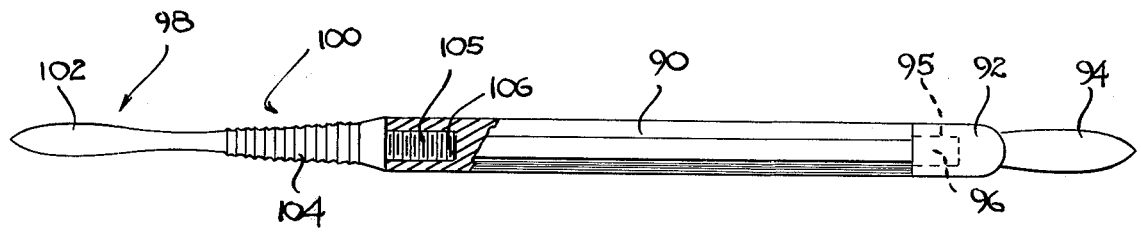
Figure 11:
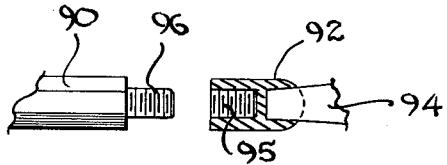
Figure 12:
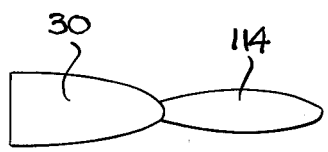
Figure 13:
Figure 14:
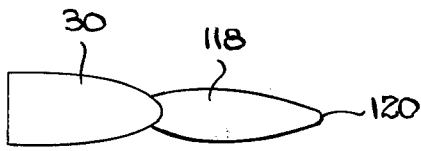
Figure 15:
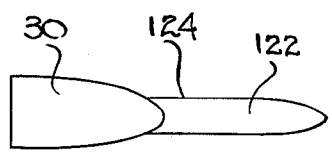
Figure 17:
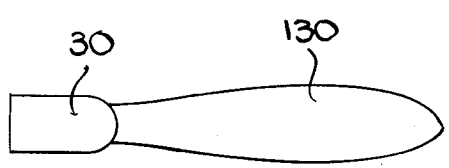
Figure 16:
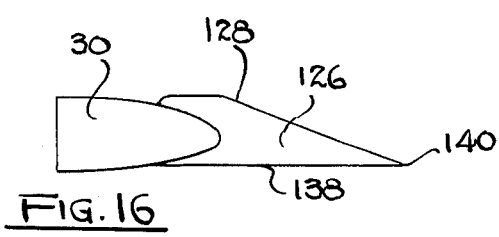

Having thus described the invention in general terms, reference will now be made to the accompanying drawings in which:

FIG. 1 is a side elevational view of a tool for forming dental restorations used in the oral cavity and which tool is constructed in accordance with and embodies the present invention;

FIG. 2 is a top plan view of the tool of FIG. 1;

FIG. 3 is a vertical sectional view taken along line 3—3 of FIG. 1, and showing the construction of the handle section forming part of the present invention;

FIG. 4 is a fragmentary vertical sectional view showing one construction of a tool section for attachment to a handle section forming part of the tool of the present invention;

FIG. 5 is a fragmentary vertical sectional view showing an alternate construction of a tool section;

FIG. 6 is a top plan view showing a portion of a serrated surface section forming part of the tool of the invention;

FIG. 7 is a side elevational view, similar to FIG. 1, and showing a modified form of tool constructed in accordance with and embodying the present invention;

FIG. 8 is a side elevational view, also similar to FIG. 2, and showing a further modified form of tool constructed in accordance with and embodying the present invention;

FIG. 9 is a fragmentary top plan view, substantially taken along line 9—9 of FIG. 8, and showing a configuration of a portion of the tool of FIG. 8;

FIG. 10 is a side elevational view, partially broken away and in section, of a further embodiment of the tool constructed in accordance with and embodying the present invention, and showing both tool sections removably attached to a handle section;

FIG. 11 is a fragmentary side elevational view showing a portion of the dental tool of FIG. 10 and, in particular, the technique for attaching a tool section head to the handle section forming part of the tool of the present invention;

FIG. 12 is a top plan view showing the construction of an alternate form of tool section forming part of the tool in accordance with the present invention;

FIG. 13 is a top plan elevational view of another alternate form of tool section in accordance with the present invention;

FIG. 14 is a top plan view of a further form of tool section in accordance with the present invention;

FIG. 15 is a top plan view of an additional form of tool section in accordance with the present invention;

FIG. 16 is a top plan view of yet another form of tool section in accordance with the present invention; and FIG. 17 is a top plan view of still another form of tool section in accordance with the present invention.

DETAILED DESCRIPTION

Referring now in more detail and by reference characters to the drawings, A designates a tool constructed in accordance with and embodying the present invention, and which is primarily useful for forming dental restorations to be used in the oral cavity of the human being. In this case, the tool of the present invention may be referred to as a "dental instrument", or a "dental tool" since tools of the present invention are primarily designed for use in creating and forming dental restorations to be used in the oral cavity.

The tool A of the present invention comprises a handle section 20 having a non-circular side wall 22, preferably of an octagonal shape. However, the shape of the side wall can adopt any geometric form including a circular side wall, although non-circular side walls, and preferably eight-sided (octagon) shaped side walls, are desired in order to facilitate gripping of the handle section 20. In addition, the handle section 20 may be serrated as shown in FIGS. 1-3 of the drawings in order to further facilitate gripping thereof by the fingers of the user of the tool. However, in this case, gripping serrations are located only on seven of the side walls with the eighth remaining relatively smooth and flat.

The handle section 20 is generally elongate in construction as illustrated and is provided at its right-hand end, reference being made to FIG. 1, with a relatively flat transverse end wall 24. In addition, the elongate handle section 20 is provided with an internally threaded recess 26 in order to threadedly, and thereby fixedly, but nevertheless removably, receive the threaded shank 28 of a head section 30. This head section 30 has essentially the same diametral size and shape as the handle section 20 and is threadedly, but nevertheless removably, secured thereto through the externally threaded shank 28 fitting within the internally threaded recess 26 formed within the handle section 20.

The head section 30 rigidly carries a first tool section 32 which is used in the formation of a dental restoration to be used in the oral cavity of a human being. This tool section 32 comprises a blade-like element 34 provided with a shank 36, the latter of which extends into, and is rigidly and retentively retained within, the head 30. In this case, the flange 36 can either be inserted into the head 30 and retained therein by means of any suitable adhesive or the like. Otherwise, the flange 36 can actually be molded into and integrally formed into the head 30 during the formation thereof.

The handle section 20 is preferably formed of a metal material of the type normally used in the construction of tools of this type and, in this case, is preferably a high tensile steel material. However, other forms of metals may be used in the construction of the handle section forming part of the tool. The head section 30 is preferably formed of a moldable plastic material, such as polyethylene, polystyrene, polybutadiene, various co-polymers thereof and the like. In this way, the head section 30 may be formed in a relatively inexpensive manner. Nevertheless, the threaded shank 28 may be removably, but nevertheless threadedly, secured in a retentive manner in the internally threaded recess 26 formed in the handle section 20. As indicated above, the tool section 32 may have a portion thereof formed within the head 30 during the formation of the latter. In addition, the flange 36 of the tool section 32 may be inserted within a slot which is formed in the head section 30 and retentively retained therein. If desired, the flange 36 may be provided with a pair of apertures 37 for the plastic to flow through during formation of the head 30 to thereby physically attach the flanges 36 to the head 30.

FIG. 5 of the present invention more fully illustrates a modified form of tool section 38 which may be used in the tool of the present invention. In this case, the tool section 38 comprises an enlarged head 40 comprised of a cylindrically shaped side wall 42 and a forward transverse end wall 44, along with a diametrally-reduced tubular boss 46 formed at the rearward end thereof. The tubular boss 46 has an externally threaded section 48 for threaded attachment to the internally threaded recess 26 formed within the handle section 20. In addition, a work member, such as a tool section 50, is provided with an outwardly extending blade 52 and a rearwardly extending shank or flange 54, the latter of which extends into the head 40 through an aperture in the front wall 44. Thereafter, the entire central cavity of the head 40 is filled with a moldable plastic through the externally threaded tubular boss 46 so that the rearwardly extending flange 54 is permanently embedded in the solid molded plastic filler 56, in the manner as further illustrated in FIG. 5. In this case, any form of structural steel may be used to form the outer head shell 40 and any form of injectable moldable plastic may be used to form the inner core 56. Again, the tool section 50 may be formed of a structural metal of the type described.

At its left-hand end, reference being made to FIGS. 1 and 2, the handle section 20 merges into a diametrally reduced neck portion 58 which integrally merges into a serrated surface section 60 which is initially diametrally enlarged with respect to the diametrally reduced neck section 58. The serrated section 60 is more fully illustrated in FIG. 6 of the drawings and is comprised of a series of axially, spaced apart, radially extending ring sections 62, each formed by a pair of radially, outwardly extending walls 64 connected by a rounded outer annular edge 66. Valleys 67 connecting each of the ring sections 62 are also rounded. Moreover, each of the edges 66 are diametrally reduced in succession relation to one another over the overall length of the external serrated section 60.

While the construction as illustrated in FIG. 6 is described herein as a preferred construction, any form of serrated surface construction may be utilized in creating a vibratory action on the dental restorations being formed. In this respect, it is important that the serrated surface section 60 be designed so that it is capable of forming a vibratory action on the dental restoration to be used in the oral cavity in order to move any fluid in the dental restoration material, typically the porcelain material, which is used in the formation of the dental restoration.

The blade 34 actually adopts the form of a posterior carver in the shape and size as illustrated in FIGS. 1 and 2 of the drawings. One of the unique aspects of the present invention is that the tool section 32 is formed so that the blade 34 is relatively thin in cross-sectional shape. Moreover, the blade 34 is formed so that it is relatively pliable and flexible, capable of being elastically deformable, but nevertheless which is capable of performing the required function in the formation of the dental restoration. In this case, it is preferable that the blade 34 be formed of a high tensile strength steel, although other structural metals could be used.

The serrated section 60 integrally merges into a second tool section 68 which adopts the form of a cutter and lifter. In this case, the second tool section 68 includes an extension 70 which extends from the serrated section 60 and integrally merges into a curved spoon-like device 72 having a relatively sharp outer edge 74. This particular tool section 68 is designed to cut and lift the dental restoration material during the formation of the dental restoration for use in the oral cavity.

FIG. 7 illustrates a modified form of dental tool constructed in accordance with and embodying the present invention. In this case, the tool illustrated in FIG. 7 is similar in many respects to the dental tool illustrated in FIGS. 1–6. However, in this embodiment, the dental tool of FIG. 7 comprises a first tool section 32 which has a work member in the form of a carver 76 extending from a head section 78, the latter of which is removably secured to the handle section 20. At the left-hand portion of the handle section 20 is located a serrated section 60, similar to the serrated section in FIG. 2. Integrally merging into the serrated section 60 is a second tool section in the form of a cutter and lifter 68 which is also similar to the cutter and lift section in FIG. 2.

FIGS. 8 and 9 illustrate yet another modified form of tool in accordance with the present invention used in the formation of dental restorations. The tool illustrated in FIGS. 8 and 9 of the drawings includes a handle section 20, with a first tool section 80 on one end thereof. In this case, the first tool section 80 includes a head 82 which is threadedly or otherwise fixedly attached to the handle section 20 and extending outwardly from the head section 82 is a work member 84, in the form of a posterior and interior carver, connected to the head section 82 by means of an extended shank 86. At its left-hand end, the handle section 20 merges into the serrated surface section 60 through the diametrally reduced neck 58 and this serrated surface section 60 integrally merges into a second tool section 88. The tool section 88 adopts a form of a lingueal shaper and carver.

FIGS. 10 and 11 illustrate an additional embodiment of the present invention in which both first and second tool sections are removably, but nevertheless fixedly, secured to a handle section. The embodiment of FIG. 10 comprises a handle section 90 similar to the previously described handle section 20. However, the handle section 90 is provided at its forward end with a head 92, the latter carrying a work member 94 which also adopts the form of an interproximal condenser. The head 92 is provided with an internally threaded recess 95 which is sized to accommodate an externally threaded shank 96 extending forwardly from the handle section 90. In this way, the head 92 is threadedly, but nevertheless removably, affixed to the handle section 90. At its rearward end, a second tool section 98 is also threadedly secured to the handle 90. In this case, the second tool section 98 comprises an elongate portion 100 comprised of a working member 102 in the form of a lingueal condenser, and connected to the head section 98 through a serrated section 104, substantially equivalent to the serrated section 60. This serrated section 104 is provided with an externally threaded shank 105, which is designed to be threadedly, but nevertheless removably, connected to an internally threaded recess 106 formed within the handle section 90 in the manner as illustrated in FIG. 10 of the drawings.

FIGS. 12–17 illustrate various forms of tool sections which may be used in the present invention. In this case, each of the tool sections illustrated in FIGS. 12–17 comprise a head substantially equivalent to the head 30 for removable attachment to the body section 20. However, the working members extending from the head differ slightly in each of these respects. FIG. 12 represents one form of work member 114 in the form of a labial condenser. FIG. 13 illustrates another form of work member 116 in the form of a labial condenser 116. FIG. 14 illustrates an additional labial condenser 118 having a flat forward edge 120. FIG. 15 illustrates a labial condenser 122 with parallel side edges 124. FIG. 16 illustrates a cutter 126 having a tapered cutting edge 128. FIG. 17 illustrates a spade 130 having approximately twice the size of any of the aforementioned work members. In each case, any of the first tool members described in connection with FIGS. 12-17 may be used in connection with any of the previously described tools of the present invention.

One of the unique aspects of the present invention is that the tool described herein is capable of being utilized in such manner that the first and second tool sections are capable of being quickly rotated and manipulated in order to perform the work on the dental restoration. In addition, the serrated surface section is located with respect to one of the tool sections so that it can be almost instantaneously moved into a position where it is capable of creating the necessary vibratory action in order to move fluid into the restoration material, such as the porcelain. In this way, the porcelain cannot irrevocably harden which would otherwise result in the destruction of the dental restoration thus formed. In essence, with the tool of the present invention, it is possible to "pack" the restoration material and vibrate this material almost simultaneously therewith in order to permit movement of the water into the restoration material in order to enable molding and shaping of the same.

It has been established in accordance with the present invention that the gypsum which forms the mold is quite porous and tends to absorb the water included in the feldspar forming the porcelain restoration material. Consequently, it is incumbent upon any technicians producing dental restorations to move fairly quickly in a manner so that the gypsum does not absorb the water, thereby rendering the feldspar fairly useless. However, the tools of the present invention are so uniquely designed so that both packing operations and shaping operations can be performed fairly quickly. In addition, the vibratory action necessary to create a movement of water into the feldspar on the thus formed dental restoration is sufficient in order to enable the operator to form the desired end product. The restorations thus formed have a dense appearance due to the ability to pack and condense the restoration material while in a fairly pliable state. In addition, the restorations have a good color appearance and good vitality. Moreover, from a standpoint of physical characteristics, the restorations have very low porosity thereby inhibiting bacteria formation and air entrapment which increases the life of the restorations.

Some of the work members used in the present invention are uniquely designed to also facilitate in the formation of the dental restorations. Particularly the carver 78 is designed so that an upper edge 132 is slightly divergent inwardly toward an axis passing through the handle section 20. A lower edge 134 is curved and merges into the upper edge 132 at a point 136. The work member 126 is also uniquely designed so that the upper edge 128 merges into a bottom edge 138 at a point 140, with the bottom edge 140 being essentially parallel to an axis passing through the handle 20.

Thus, there has been illustrated and described a unique and novel instrument used in creating dental restorations for use in the oral cavity along with a method of using the same and a method of making the same. It should be understood that many changes, modifications, variations and other uses and applications will become apparent to those skilled in the art after considering this specification and the accompanying drawings. Therefore, any and all such changes, modifications, variations and other uses and applications are deemed to embodied by this invention which is limited only by the following claims.

Having thus described my invention, what I desire to claim and secure by Letters Patent is:

1. A tool for forming dental restorations used in the oral cavity of a human being and which dental restorations are formed from a composition comprised of a hardenable material and a liquid and which will harden when the liquid is substantially removed therefrom, said tool comprising an elongate handle section capable of being grasped by the fingers of the user thereof, a first tool section on one portion of said handle section used in the formation of dental restorations from a synthetic restoration material, a second tool section on another portion of said handle section cooperatable with said first tool section and used in the formation of the dental restorations from the synthetic restoration material and which first and second tool sections are used in combination to form the dental restorations, and a serrated surface section associated with said elongate handle section and being located in very close proximity to said first tool section and substantially spaced from said second tool section along the length of said handle section, said serrated section being comprised of a plurality of axially spaced apart radially extending ring elements having rounded outer edges which are separated by rounded recessed grooved portions, each of said ring elements being diametrally reduced in successive relationship to one another over the overall length of serrated surface section such that the largest of said ring elements is spaced furthest from the first tool section and the smallest of the ring sections is located closest to the first tool section, said serrated surface section being effective in creating vibratory action on the composition during molding thereof to form the dental restorations through reciprocative movement to further aid in the retention of the liquid in the hardenable material during the formation of the dental restorations, said serrated surface section being located relative to said first tool section so that the serrated section may be immediately shifted axially toward said dental restorations after action by said first tool section, and said first tool section being axially located with respect to said handle section so that said dental tool may be rotated through approximately a 180° arc to utilize both said first and second tool sections and such that said serrated surface section may be quickly and easily located in proximity to the dental restorations to cause an additional vibratory action thereon.

2. The tool of claim 1 further characterized in that said first tool section is located at one end of said handle section and said second tool section is located at an opposite end thereof.

3. The tool of claim 1 further characterized in that the first tool section is designed with a size and shape to pick up the synthetic restoration material and place the same in proper position.

4. The tool of claim 3 further characterized in that the second tool section is designed with a size and shape to carve and shape the restoration.

5. The tool of claim 3 further characterized in that the second tool section is designed with a size and shape to condense the synthetic restoration material.

6. The tool of claim 1 further characterized in that said rings are formed of circumferentially extending ridges, each having outwardly and inwardly tapering side walls terminating in outer rounded edge portions.

7. The tool of claim 1 further characterized in that said first tool section comprises a carving blade having an upper edge slightly divergent inwardly toward a central axis passing through said handle section and a lower curved edge merging into the upper edge at a point.

8. The tool of claim 1 further characterized in that said first tool section comprises a carving blade with an upper edge diverging toward a central axis passing through said handle section and merging into a bottom edge which is essentially parallel to said axis.

9. A tool for forming dental restorations used in the oral cavity of a human being and which dental restorations are formed from a composition comprised of a hardenable material and a liquid and which will harden when the liquid is substantially removed therefrom, said tool comprising an elongate handle section capable of being grasped by the fingers of the user thereof, a first tool section on one end of said handle section used in the formation of dental restorations from snythetic restoration material, said handle section having a first threaded attachment means, said first tool section comprising a head portion, said head portion having a second threaded attachment means cooperatable with said first attachment means to fixedly, but nevertheless removably, secure said head portion to said handle section, and said first tool section being fixedly attached to said head portion, a second tool section on an opposite end of said handle section cooperatable with said first tool section and used in the formation of the dental restorations from the synthetic restoration material and which first and second tool sections are used in combination to form the dental restorations, and a serrated surface section associated with said elongate handle section and being located in very close proximity to said first tool section and substantially spaced from said second tool section along the length of said handle section, said serrated surface section being effective in creating vibratory action on the composition during molding thereof to form the dental restorations through reciprocative movement of further aid in the retention of the liquid in the hardenable material during the formation of the dental restorations, said serrated surface section being located relative to said first tool section so that the serrated section may immediately be shifted axially toward said dental restorations after action by said first tool section, and said first tool section being axially located with respect to said handle section so that said dental tool may be rotated through approximately a 180° arc to utilize both said first and second tool sections such that said serrated surface section may be quickly and easily located in proximity to the dental restorations to cause an additional vibratory action thereon.

10. The tool of claim 9 further characterized in that said first threaded attachment means comprises a threaded shank on said handle section and said second attachment means comprises an internally threaded recess in said head portion.

11. The tool of claim 9 further characterized in that said first threaded attachment means comprises an internally threaded recess in said handle section, and said second threaded attachment means comprises a threaded shank on said head portion.

12. The tool of claim 9 further characterized in that said second tool section is also threadedly attached to said handle section.

13. The tool of claim 9 further characterized in that said second tool section is integrally secured to said handle section.

14. The tool of claim 9 further characterized in that said handle section is non-circular in cross section to facilitate handling thereof, and said handle section is provided with a plurality of serrations thereon to further aid in facilitating handling thereof.

15. The tool of claim 9 further characterized in that said serrated surface section is comprised of a plurality of axially spaced apart radially extending ring elements having rounded outer edges which are separated by rounded recessed grooved portions, each of said ring elements being diametrally reduced in successive relationship to one another over the overall length of serrated surface section such that the largest of said ring elements is spaced furthest from the first tool section and the smallest of the ring sections is located closest to the first tool section.

16. A method of using a tool for forming dental resto-rations used in the oral cavity of a human being where the tool is comprised of a handle section, a first tool section at one end thereof and a second tool section at the other end thereof, and with a serrated surface section located in close proximity to said first tool section and spaced substantially from said second tool section along the length of said handle section, and where said dental restorations are formed from a composition comprised of a hardenable material and a liquid and which will harden when the liquid is substantially removed therefrom, said method comprising engaging the handle section of the tool and locating the first tool section on one end thereof in relation to a mold means to perform a first operation in the formation of the dental restoration by applying the synthetic restoration composition to the mold means, shifting the position of the dental tool to locate the serrated surface section thereon in proximity to the dental restoration being formed, moving the serrated section on the restoration composition thus formed to cause a vibratory action in the composition and thereby cause movement of liquid relative to the synthetic restoration composition and entrainment of liquid in the composition during formation of the restoration, rotating the dental tool through an approximately 180° arc to locate a second tool section in proximity to the dental restoration being formed, and operating on the dental restoration with said second tool section.

17. The method of using a dental tool of claim 16 further characterized in that said method comprises reciprocatively moving said serrated surface section across said dental restoration thus formed in order to cause liquid movement with respect to the restoration composition and liquid entrainment in the composition.

18. The method of using a dental tool of claim 16 further characterized in that the first tool section is designed with a size and shape to pick up the synthetic restoration material and place the same in proper position.

19. The method of using a dental tool of claim 16 further characterized in that the second tool section is designed with a size and shape to carve and shape the restoration.

20. A tool for forming dental restorations used in the oral cavity of a human being and which dental restorations are formed from a composition comprised of a hardenable material and a liquid and which will harden when the liquid is substantially removed therefrom, said tool comprising an elongate handle section capable of being grasped by the fingers of the user thereof, a first tool section on one end of said handle section used in the formation of dental restorations from synthetic restoration material, said handle section having a first threaded attachment means, said first tool section comprising a head portion, said head portion having a second threaded attachment means cooperatable with said first attachment means to fixedly, but nevertheless removably, secure said head portion to said handle section, and said first tool section being fixedly attached to said head portion, a second tool section on an opposite end of said handle section cooperatable with said first tool section and used in the formation of the dental restorations from the synthetic restoration material and which first and second tool sections are used in combination to form the dental restorations, and a serrated surface section associated with said elongate handle section and being located in very close proximity to said first tool section and substantially spaced from said second tool section along the length of said handle section, said serrated section being comprised of a plurality of axially spaced apart radially extending ring elements having rounded outer edges which are separated by rounded recessed grooved portions, each of said ring elements being diametrally reduced in successive relationship to one another over the overall length of serrated surface section such that the largest of said ring elements is spaced furthest from the first tool section and the smallest of the ring sections is located closest to the first tool section, said serrated surface section being located relative to said first tool section so that the serrated section may be immediately shifted axially toward said dental restorations after action by said first tool section, and said first tool section being axially located with respect to said handle section so that said dental tool may be rotated through approximately a 180° arc to utilize both said first and second tool sections and such that said serrated surface section may be quickly and easily located in proximity to the dental restorations to cause an additional vibratory action thereon.

21. A tool for forming dental restorations used in the oral cavity of a human being and which dental restorations are formed from a composition comprised of a hardenable material and a liquid and which will harden when the liquid is substantially removed therefrom, said tool comprising an elongate handle section capable of being grasped by the fingers of the user thereof, a first tool section on one end of said handle section used in the formation of dental restorations from synthetic restoration material, said handle section having an attachment means, said first tool section comprising a head portion, said head portion having a second attachment means cooperatable with said first attachment means to fixedly secure said head portion to said handle section, and said first tool section being fixedly attached to said head portion, a second tool section on an opposite end of said handle section cooperatable with said first tool section and used in the formation of the dental restorations from the synthetic restoration material and which first and second tool sections are used in combination to form the dental restorations, said first and second tool sections being of different size and shape but being designed to perform essentially the same operative function in forming the dental restorations, and a serrated surface section associated with said elongate handle section and being located in very close proximity to said first tool section and substantially spaced from said second tool section along the length of said handle section, said serrated surface section being effective in creating vibratory action on the composition during molding thereof to form the dental restorations through reciprocative movement to further aid in the retention of the liquid in the hardenable material during the formation of the dental restorations, said serrated surface section being located relative to said first tool section so that the serrated section may immediately be shifted axially toward said dental restorations after action by said first tool section, and said first tool section being axially located with respect to said handle section so that said dental tool may be rotated through approximately a 180° arc to utilize both said first and second tool sections such that said serrated surface section may be quickly and easily located in proximity to the dental restorations to cause an additional vibratory action thereon.

22. The tool of claim 21 further characterized in that said first tool section is relatively thin in cross section so that it is relatively pliable and flexible to be elastically deformable and which is also capable of performing a carving function, said first tool section being curved into a spoon-like area having arcuate outer edges merging into an outermost point which is located upwardly of the major portion of said spoon-like area.

23. The tool of claim 21 further characterized in that said first tool section comprises a carving blade having an upper edge slightly divergent downwardly and outwardly toward a central axis passing through said handle section and a lower curved edge merging into the upper edge at an outermost point.

24. The tool of claim 21 further characterized in that said first tool section comprises a carving blade with an upper edge diverging downwardly and outwardly toward a central axis passing through said handle section and merging into a bottom edge which is essentially parallel to said axis at an outermost point below the central axis of said handle.

25. The tool of claim 21 further characterized in that said first tool section comprises a blade having an upper edge and a long edge which are parallel to each other, said upper and lower edges having slightly divergent portions inwardly and forwardly of said handle section toward a central axis passing through said handle section and merging toward each other at a terminal area in proximity of said central axis.

26. The tool of claim 25 further characterized in that said terminal area is a slightly arcuate terminal area.

27. The tool of claim 25 further characterized in that said terminal area is a sharp pointed outer terminal area.

28. The tool of claim 21 further characterized in that said first tool section comprises a blade with an upper edge having an upper curved edge extending along a central axis passing through said handle section and diverging toward a central axis passing through said handle section and having a lower curved edge extending below a central axis passing through said handle section and merging into an outer portion which is essentially parallel to said axis.

* * * * *